United States Patent
Kubota et al.

(10) Patent No.: US 9,784,856 B2
(45) Date of Patent: Oct. 10, 2017

(54) RADIOGRAPHIC IMAGE CAPTURING APPARATUS

(71) Applicant: Konica Minolta, Inc., Tokyo (JP)

(72) Inventors: Tetsuo Kubota, Kokubunji (JP); Akira Hiroshige, Kokubunji (JP); Takanori Kakigi, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/426,511

(22) Filed: Feb. 7, 2017

(65) Prior Publication Data

US 2017/0248706 A1 Aug. 31, 2017

(30) Foreign Application Priority Data

Feb. 25, 2016 (JP) ................................. 2016-034024

(51) Int. Cl.
*G01T 1/24* (2006.01)
*A61B 6/00* (2006.01)

(52) U.S. Cl.
CPC ................ *G01T 1/244* (2013.01); *A61B 6/56* (2013.01)

(58) Field of Classification Search
CPC ..... A61B 6/56; A61B 2560/0214; G01T 1/00; G01T 1/244; G01T 1/175
See application file for complete search history.

(56) References Cited

U.S. PATENT DOCUMENTS

| | | | |
|---|---|---|---|
| 2004/0252613 A1* | 12/2004 | Iwakiri | G03B 42/02 369/53.12 |
| 2006/0202127 A1* | 9/2006 | Ozeki | G01T 1/2018 250/370.01 |
| 2012/0133339 A1* | 5/2012 | Eguchi | A61B 6/00 320/162 |
| 2015/0117614 A1* | 4/2015 | Kim | A61B 6/4405 378/102 |

FOREIGN PATENT DOCUMENTS

JP 2015167449 A 9/2015

* cited by examiner

*Primary Examiner* — Marcus Taningco
(74) *Attorney, Agent, or Firm* — Lucas & Mercanti, LLP

(57) ABSTRACT

A radiographic image capturing apparatus includes the following. A connector coupling detector detects coupling between an external connector and a connector of the radiographic image capturing apparatus. A power supply detector detects an available state of external electric power. A controller controls a turned-on and a turned-off state of the radiographic image capturing apparatus. At a timing when the power supply detector detects a change from the available state to the unavailable state of the external electric power, the controller turns off the radiographic image capturing apparatus if the connector coupling detector detects the coupling between the external connector and the connector of the radiographic image capturing apparatus, or the controller maintains the turned-on state if the connector coupling detector detects the uncoupling between the external connector and the connector of the radiographic image capturing apparatus.

7 Claims, 6 Drawing Sheets

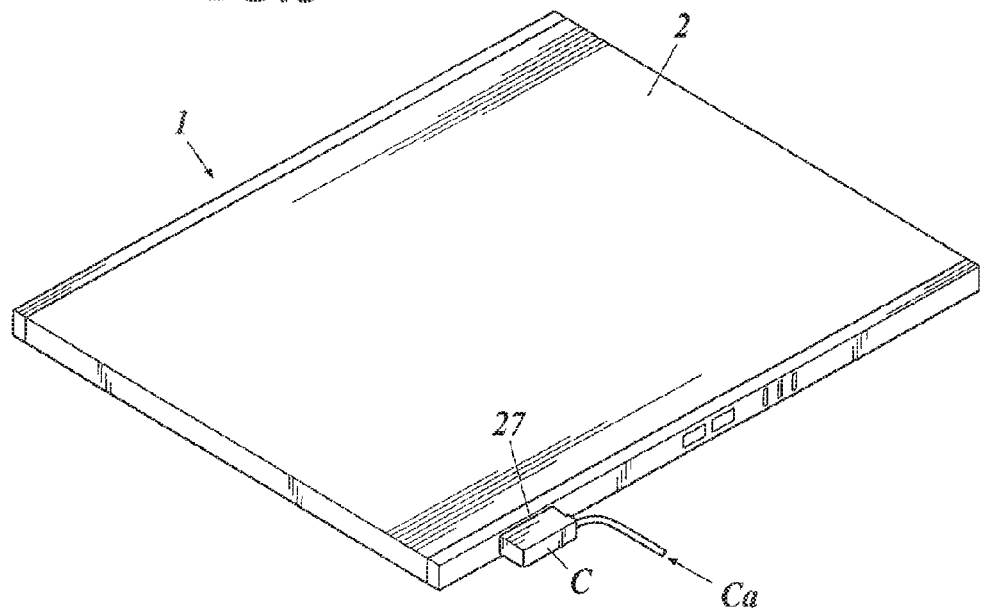
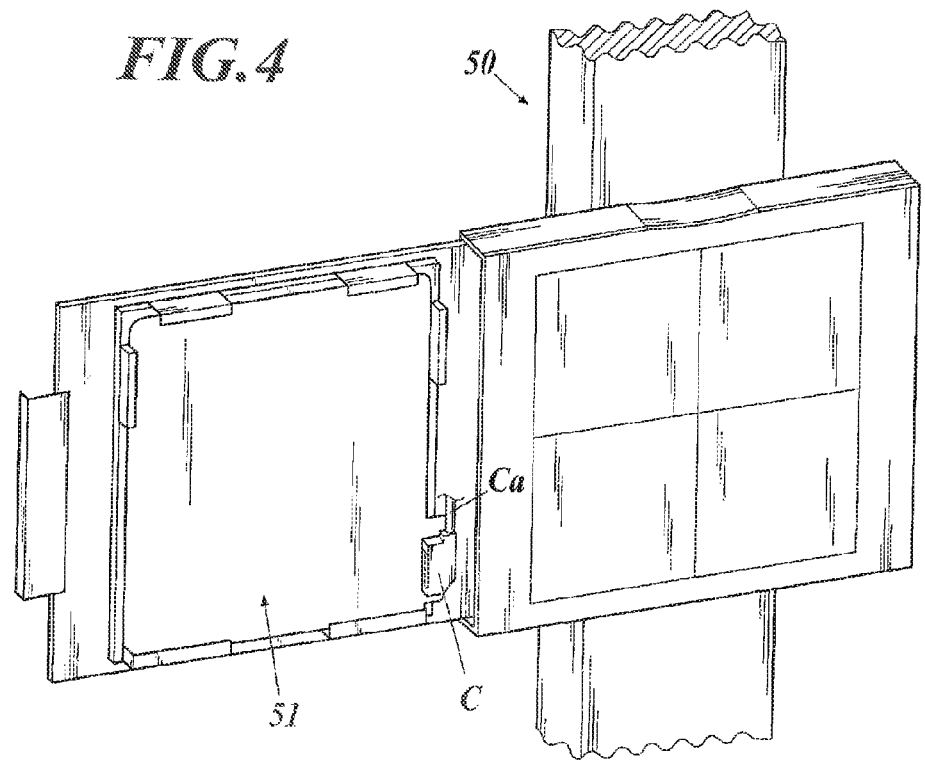

RADIOGRAPHIC IMAGE CAPTURING APPARATUS

BACKGROUND OF THE INVENTION

Field of the Invention

The present invention relates to radiographic image capturing apparatuses, in particular to a radiographic image capturing apparatus that can control turning on/off thereof.

Description of Related Art

Various types of radiographic image capturing apparatuses (flat panel detectors) have been developed each including a two-dimensional array (matrix) of radiation detecting elements, converting radiation passing through a subject into signal values in proportion to the dose of the radiation at the radiation detecting elements, and reading the signal values from the radiation detecting elements. Portable radiographic image capturing apparatuses also have been recently launched each including radiation detecting elements accommodated in a housing (for example, refer to Japanese Unexamined Patent Application Publication No. 2015-167449).

A radiographic image capturing apparatus may be mounted on a capturing table in a capturing room of a facility, such as a hospital, for radiographic image capturing of, for example, a breast region. The radiographic image capturing apparatus may also be detached from the capturing table to be placed on the body of a subject or patient or between a bed and a patient lying on the bed for radiographic image capturing.

For the use of the radiographic image capturing apparatus in a limited space, for example, in an in-vehicle radiographic image capturing system in a medical cart, the radiographic image capturing apparatus may be fixed in a cassette holder with screws. To eliminate the need for troublesome removal of the screws by an operator, such as a radiological technician before turning on/off of the radiographic image capturing apparatus, some radiographic image capturing apparatuses are configured to be turned on/off automatically in cooperation with switching on/off of an external device that supplies electric power to the radiographic image capturing apparatus.

The same configuration is applied to the radiographic image capturing apparatus mounted on the capturing table in the capturing room. Some radiographic image capturing apparatuses are configured to be automatically turned on/off in cooperation with switching on/off of a console connected to the radiographic image capturing apparatus with, for example, a cable, or switching on/off of a relay for communication between the radiographic image capturing apparatus and the console.

For example, at the end of radiographic image capturing with the radiographic image capturing apparatus mounted on the capturing table in the capturing room, the radiographic image capturing apparatus having such a configuration described above is automatically turned off in cooperation with switching off of the console or relay even if the operator or radiological technician forgets to turnoff the radiographic image capturing apparatus. This configuration advantageously prevents consumption of electric power in the radiographic image capturing apparatus that is failed to be turned off.

Unfortunately, the radiographic image capturing apparatus that is configured to be inevitably turned off in cooperation with the switching off of the device (for example, external devices such as the console or relay described above) connected to the radiographic image capturing apparatus has the following disadvantages: For example, even if the operator or radiological technician manually turns on the radiographic image capturing apparatus connected to the device (for example, external devices such as the console or relay described above) in the switched-off state, the radiographic image capturing apparatus may be automatically turned off in cooperation with the switching-off state of the device.

Such automatic turning off of the radiographic image capturing apparatus against the intention of the operator or a radiological technician may make the operator feel that the radiographic image capturing apparatus is difficult to use.

When the radiographic image capturing apparatus attached to the capturing table and used in capturing (in the turned-on state) is detached from the capturing table for radiographic image capturing of, for example, a knee joint of a patient, the connector of the radiographic image capturing apparatus may be uncoupled from the connector of the capturing table, stopping the power supply to the radiographic image capturing apparatus. In such a case, the radiographic image capturing apparatus may be automatically turned off under the misinterpretation of the stop of the power supply as the switching off of the device.

Since the radiographic image capturing apparatus is turned off against the intention of the operator or radiological technician to conduct radiographic image capturing of, for example, a knee joint of a patient with the radiographic image capturing apparatus detached from the capturing table, the operator is forced to turn on the radiographic image capturing apparatus again. This also makes the operator to feel that the radiographic image capturing apparatus is difficult to use.

BRIEF SUMMARY OF THE INVENTION

An object of the present invention, which has been made in view of the problems described above, is to provide a user-friendly radiographic image capturing apparatus that can properly control the turning on/off thereof depending on the situation.

According to one aspect of the present invention, there is provided a radiographic image capturing apparatus including: a two-dimensional array of radiation detecting elements; a connector couplable to an external connector; a connector coupling detector to detect coupling or uncoupling between the external connector and the connector of the radiographic image capturing apparatus; a power supply detector to detect an available state or an unavailable state of external electric power fed through the external connector; and a controller to control a turned-on state and a turned-off state of the radiographic image capturing apparatus, wherein at a timing when the power supply detector detects a change from the available state to the unavailable state of the external electric power, the controller turns off the radiographic image capturing apparatus in the turned-on state if the connector coupling detector detects the coupling between the external connector and the connector of the radiographic image capturing apparatus, or the controller maintains the turned-on state of the radiographic image capturing apparatus if the connector coupling detector detects the uncoupling between the external connector and the connector of the radiographic image capturing apparatus.

BRIEF DESCRIPTION OF THE DRAWINGS

The present invention will become more fully understood from the detailed description given hereinbelow and the appended drawings, and thus are not intended to define the limits of the present invention, and wherein;

FIG. 3 illustrates the radiographic image capturing apparatus having a connector coupled with an external connector;

FIG. 4 illustrates an exemplary configuration of a capturing table and an external connector provided in the capturing table;

DETAILED DESCRIPTION OF PREFERRED EMBODIMENTS

Embodiments of a radiographic image capturing apparatus according to the present invention will now be described with reference to the accompanying drawings.

[Configuration of Radiographic Image Capturing Apparatus]

Figure 1:
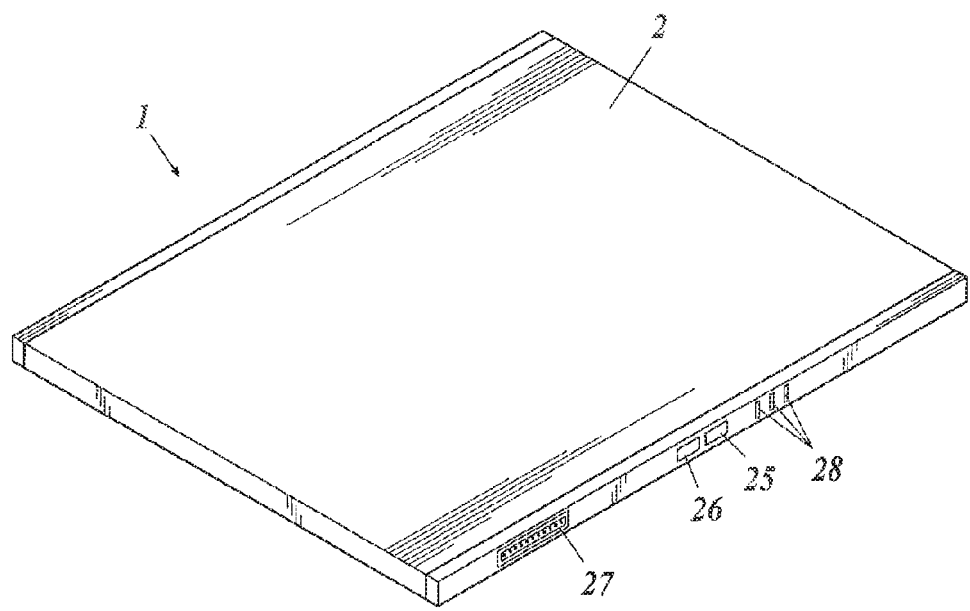
FIG. 1 is an external perspective view of a radiographic image capturing apparatus.
Figure 2:
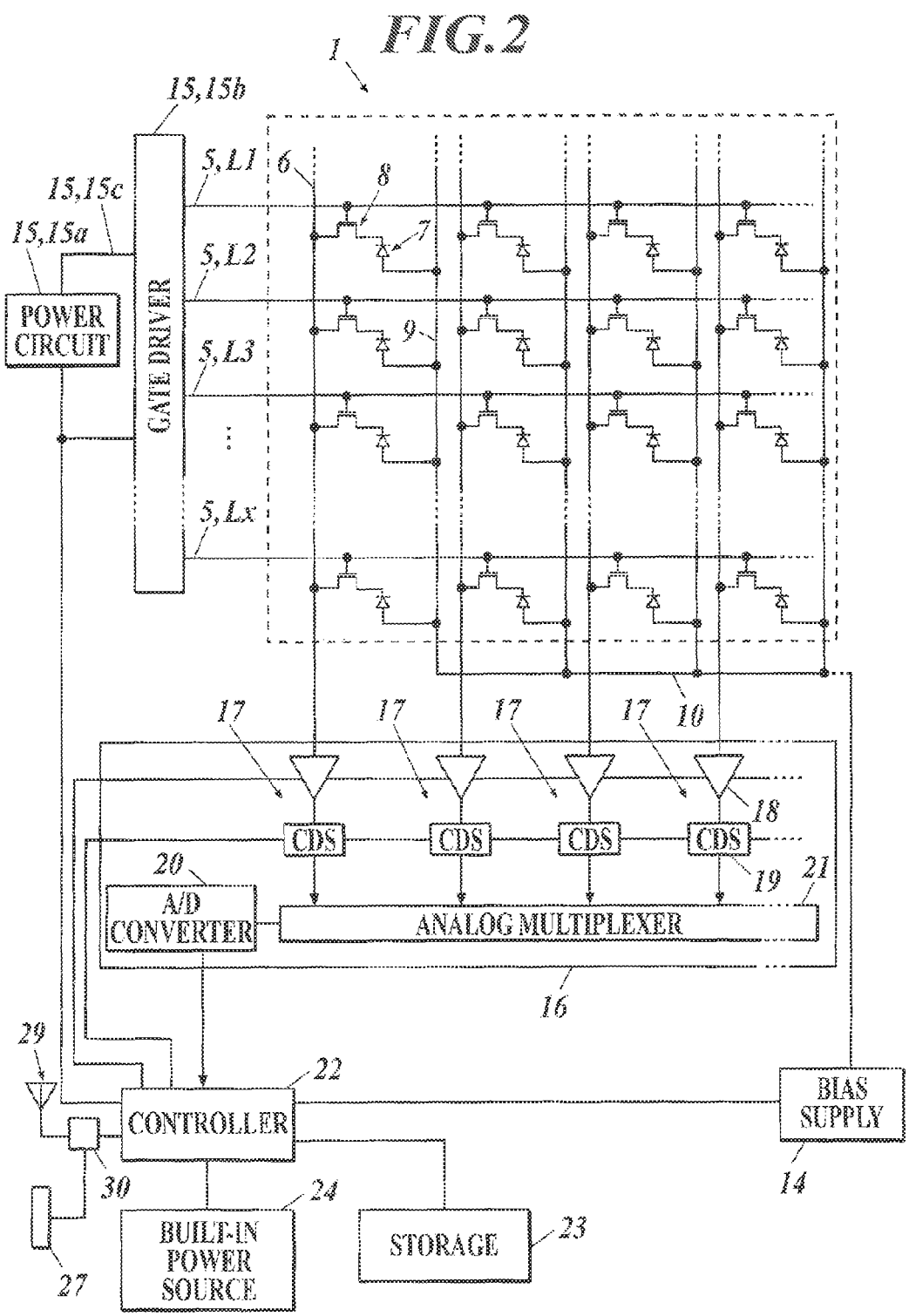
FIG. 2 is a block diagram of an equivalent circuit in the radiographic image capturing apparatus.

FIG. 1 is an external perspective view of a radiographic image capturing apparatus 1, and FIG. 2 is a block diagram of an equivalent circuit in the radiographic image capturing apparatus 1. In this embodiment, the radiographic image capturing apparatus 1 includes a housing 2 (refer to FIG. 1) accommodating radiation detecting elements 7 (refer to FIG. 2).

With reference to FIG. 1, the housing 2 of the radiographic image capturing apparatus 1 has a power switch 25, a changing-over switch 26, a connector 27, an indicator 28, and the like on one side face. The housing 2 further has an antenna 29 (refer to FIG. 2) for establishing wireless communication with an external device, on the opposite side face (not shown).

In use, the radiographic image capturing apparatus 1 may be mounted on a capturing table 50 (refer to FIG. 4) or a cassette holder in a medical cart, as is described in the background art. The radiographic image capturing apparatus 1 also may be used independently from the capturing table 50; for example, the radiographic image capturing apparatus 1 may be disposed on a subject or patient or between a bed and a patient lying on the bed for radiographic image capturing.

With reference to FIG. 2, the housing 2 of the radiographic image capturing apparatus 1 according to the embodiment accommodates a two-dimensional array (matrix) of radiation detecting elements 7 disposed on a sensor substrate (not shown). Each radiation detecting element 7 is connected to a bias line 9. Each radiation detecting element 7 receives a reverse bias voltage from a bias supply 14 through the bias line 9 and a connection 10 connected to the bias line 9.

Each radiation detecting element 7 is connected to a thin film transistor (TFT) 8, which functions as a switching element. Each TFT 8 is connected to a signal line 6. The radiation detecting elements 7 generate electric charges in proportion to the dose of radiation passing through a subject (not shown).

ON-voltage and OFF-voltage applied from a power circuit 15a through an interconnection 15c are switched at a gate driver 15b in a scan driving unit 15 and the switched voltage is applied to each of the scanning lines 5(L1) to 5(Lx). Upon application of the OFF-voltage through the scanning lines 5, each TFT 8 is switched off and interrupts conduction between the radiation detecting element 7 and the signal line 6 to accumulate electric charge in the radiation detecting element 7. Upon application of ON-voltage through the scanning lines 5, each TFT 8 is switched on and discharges the electric charge accumulated in the radiation detecting element 7 to the signal line 6.

Each signal line 6 is connected to a readout circuit 17 in a readout IC 16. A process of reading signal values D is started with sequential application of ON-voltage from the gate driver 15b to the scanning lines 5(L1) to 5(Lx). The TFTs 8 are thereby switched on, and the electric charges accumulated in the radiation detecting elements 7 flow through the TFTs 8 and the signal lines 6 into the readout circuits 17, and the amplifying circuits 18 output voltage values in proportion to the electric charges flown into the amplifying circuits 18.

Correlated double sampling circuits 19 (each indicated with "CDS" in FIG. 2) read the voltage values received from the amplifying circuits 18 and output the voltage values in the form of analog signal values D. The signal values D output from the CDS circuits 19 are sequentially transmitted through an analog multiplexer 21 to an A/D converter 20, converted into digital signal values D at the A/D converter 20, and stored in a storage 23.

A controller 22 includes a central processing unit (CPU), a read-only memory (ROM), a random-access memory (RAM), a computer having a bus connected to, for example, an input-output interface, a field programmable gate array (FPGA), and any other components that are not shown in the drawings. The controller 22 may be a dedicated controlling circuit.

The controller 22 is connected to the storage 23, which may be a static RAM (SRAM), a synchronous DRAM (SDRAM), or a NAND flash memory, and a built-in power source 24, which may be a lithium ion capacitor. The controller 22 is also connected to a communication unit 30 for establishing wireless and physical communication with an external device via the antenna 29 and the connector 27 described above.

The controller 22 controls the application of a reverse bias voltage from the bias supply 14 to each radiation detecting element 7 and the operations of the scan driving unit 15 and the readout circuits 17 as described above, so that the signal values D are read from the radiation detecting elements 7 and stored in the storage 23. The controller 22 also controls the transfer of the signal values D stored in the storage 23 to an external device via the communication unit 30.

The controller 22 can conduct on/off control to the radiographic image capturing apparatus 1. The controller 22 includes a microcomputer (not shown) that can be driven with a low electric power from a built-in power source 24 in the radiographic image capturing apparatus 1 in the turned-off state. The controller 22 can turn on the radiographic image capturing apparatus 1 from the turned-off state even while the radiographic image capturing apparatus 1 is being turned off as described in detail below.

[Detection of Coupling Between External Connector and Connector of Radiographic Image Capturing Apparatus]

In this embodiment, the connector 27 of the radiographic image capturing apparatus 1 can be coupled to an external connector C at the front end of a cable Ca, as illustrated in FIG. 3. When the radiographic image capturing apparatus 1 is mounted on the cassette holder of the capturing table 50 or the medical cart, the connector 27 (not shown in FIG. 4) of the radiographic image capturing apparatus 1 is automatically coupled to the external connector C disposed on the cassette holder 51 of the capturing table 50 illustrated in FIG. 4.

The radiographic image capturing apparatus 1 can be supplied with electric power from the external device (not shown) through the external connector C, the cable Ca, and any other component. Examples of the external device (not shown) to supply the electric power to the radiographic image capturing apparatus 1 include an external power source, an external charging device, and a relay for power supply from the power source or charging device to the radiographic image capturing apparatus 1.

In this embodiment, the external connector C includes chips therein. While the external connector C is coupled with the connector 27 of the radiographic image capturing apparatus 1, the chips of the external connector C send response signals to the radiographic image capturing apparatus 1 in response to pulsed signals from the radiographic image capturing apparatus 1.

The controller 22 of the radiographic image capturing apparatus 1 according to the embodiment is configured to transmit the pulsed signals to the external connector C for the reason described above. If the controller 22 receives the response signals from the external connector C in response to the transmission of the pulsed signals, the controller 22 detects coupling between the external connector C and the connector 27 of the radiographic image capturing apparatus 1. If the controller 22 receives no response signal from the external connector C in response to the transmission of the pulsed signals, the controller 22 detects uncoupling between the external connector C and the connector 27 of the radiographic image capturing apparatus 1.

The radiographic image capturing apparatus 1 is provided with the controller 22 that detects the coupling or uncoupling between the external connector C and the connector 27 of the radiographic image capturing apparatus 1 in response to the response signals, as described above. Alternatively, the radiographic image capturing apparatus 1 may be provided with any other component which detects physical coupling (or uncoupling) between the external connector C and the connector 27 of the radiographic image capturing apparatus 1 and transmits a signal indicating the detection of the coupling (or uncoupling) to the controller 22.

[Detection of Available State or Unavailable State of External Electric Power Fed Through External Connector]

The controller 22 of the radiographic image capturing apparatus 1 detects an available state and an unavailable state of the external electric power fed through the external connector C. The detection will now be explained in detail.

Under the condition where the connector 27 of the radiographic image capturing apparatus 1 is coupled with the external connector C and the radiographic image capturing apparatus 1 can be supplied with electric power from the external device, the electric power maybe fed to the controller 22 of the radiographic image capturing apparatus 1 in the following two modes.

[Mode 1]

The controller 22 of the radiographic image capturing apparatus 1 may be supplied with the electric power from the external device. In this case, the electric power from the external device is converted into a predetermined voltage at a power circuit (not shown) in the radiographic image capturing apparatus 1 and the voltage is applied to the controller 22. In this mode, the controller 22 is not supplied with the electric power from the built-in power source 24 (refer to FIG. 2) in the radiographic image capturing apparatus 1. During the turned-on state, the radiographic image capturing apparatus 1 continues to be supplied with the electric power from the external device.

[Mode 2]

The controller 22 in the radiographic image capturing apparatus 1 may be supplied with the electric power from the built-in power source 24 of the radiographic image capturing apparatus 1, and the built-in power source 24 may be charged with the external electric power, when needed. In this mode, the external electric power is fed to the radiographic image capturing apparatus 1 only at the time of need for charging the built-in power source 24 of the radiographic image capturing apparatus 1, even while the radiographic image capturing apparatus 1 is being turned on. The external electric power is not fed to the radiographic image capturing apparatus 1 if the built-in power source 24 is sufficiently charged.

In Mode 1, if the external device is switched off and thus cannot feed electric power to the radiographic image capturing apparatus 1, the power supply from the external device to the radiographic image capturing apparatus 1 is stopped. In addition, if the external connector C is uncoupled from the connector 27 of the radiographic image capturing apparatus 1 and the external device thus cannot feed electric power to the radiographic image capturing apparatus 1, the power supply from the external device to the radiographic image capturing apparatus 1 is stopped.

In Mode 1, detection of the stop of the power supply from the external device to the radiographic image capturing apparatus 1 indicates that the external electric power fed through the external connector C is unavailable, even though the reason for the stop of the power supply is not clear. Detection of the power supply from the external device to the radiographic image capturing apparatus 1 indicates that the external electric power fed through the external connector C is available.

Accordingly, in Mode 1, the controller 22 of the radiographic image capturing apparatus 1 can detect the available state or the unavailable state of the external electric power fed through the external connector C to the radiographic image capturing apparatus 1 based on the power supply from the external device to the radiographic image capturing apparatus 1.

In contrast, in Mode 2, even if the electric power is available from the external device to the radiographic image capturing apparatus 1 (in other words, even if the external device is in the switched-on state and the external connector C is coupled with the connector 27 of the radiographic image capturing apparatus 1), the external electric power is not fed to the built-in power source 24 sufficiently charged.

Unlike Mode 1, it is difficult in Mode 2 to detect the available state or the unavailable state of the external electric power fed through the external connector C based on the power supply from the external device to the radiographic image capturing apparatus 1. To overcome such a disadvantage, the radiographic image capturing apparatus 1 according to the embodiment has the following configuration.

The external connector C includes a microcomputer (not shown) therein. If the external connector C is coupled with the connector 27 of the radiographic image capturing apparatus 1 and the external electric power is available through the external connector C to the radiographic image capturing apparatus 1, the microcomputer in the external connector C transmits a signal indicating that the power supply to the radiographic image capturing apparatus 1 is available (hereinafter referred to as a "power-supply signal"). If the power supply from the external device through the external connector C to the radiographic image capturing apparatus 1 is stopped, the microcomputer transmits a signal indicating the power supply to the radiographic image capturing apparatus 1 is stopped (hereinafter referred to as a "supply-stop signal").

In response to reception of the power-supply signal from the microcomputer of the external connector C, the controller 22 of the radiographic image capturing apparatus 1 according to the embodiment detects the available state of the external electric power fed through the external connector C. In response to reception of the supply-stop signal or no reception of the power-supply signal nor supply-stop signal from the microcomputer of the external connector C, the controller 22 of the radiographic image capturing apparatus 1 detects the unavailable state of the external electric power fed through the external connector C.

Such a configuration allows the controller 22 of the radiographic image capturing apparatus 1 according to the embodiment to detect the available state or the unavailable state of the external electric power fed through the external connector C in both Modes 1 and 2 based on identical logical configuration parameters (i.e., based on an identical program).

In Mode 1, the controller 22 of the radiographic image capturing apparatus 1 may detect the available state or the unavailable state of the external electric power fed through the external connector C based on the power supply from the external device through the external connector C to the radiographic image capturing apparatus 1.

[On/Off Control to Radiographic Image Capturing Apparatus with Controller]

Now described is on/off control to the radiographic image capturing apparatus 1 according to the embodiment with the controller 22.

[Determination of Control to Turn Off Radiographic Image Capturing Apparatus in Turned-On State]

At a timing when (or immediately after) the change from the available state to the unavailable state of the external electric power is detected, the controller 22 of the radiographic image capturing apparatus 1 according to the embodiment determines whether the radiographic image capturing apparatus 1 in the turned-on state is to be turned off.

The controller 22 of the radiographic image capturing apparatus 1 according to the embodiment conducts such determination only at the above timing (i.e., when the change from the available state to the unavailable state of the external electric power is detected). In other words, the controller 22 of the radiographic image capturing apparatus 1 does not determine whether the radiographic image capturing apparatus 1 is to be turned off at other timings.

In this embodiment, if the controller 22 of the radiographic image capturing apparatus 1 detects the coupling between the external connector C and the connector 27 of the radiographic image capturing apparatus 1 at the above timing, the controller 22 turns off the radiographic image capturing apparatus 1 in the turned-on state.

If the controller 22 of the radiographic image capturing apparatus 1 detects the uncoupling between the external connector C and the connector 27 of the radiographic image capturing apparatus 1 at the above timing, the controller 22 maintains the turned-on state of the radiographic image capturing apparatus 1 (i.e., keeps the radiographic image capturing apparatus 1 turned on).

[Operation]

An operation of the radiographic image capturing apparatus 1 according to the embodiment will now be described.

[Operation to Turn Off Radiographic Image Capturing Apparatus in Cooperation with Switching Off of External Device]

If the radiographic image capturing apparatus 1 is in the turned-on state at the above timing when the controller 22 of the radiographic image capturing apparatus 1 detects the change from the available state to the unavailable state of the external electric power, the controller 22 of the radiographic image capturing apparatus 1 checks for coupling between the external connector C and the connector 27 of the radiographic image capturing apparatus 1. If the controller 22 detects the coupling between the external connector C and the connector 27 of the radiographic image capturing apparatus 1 at the first timing, the reason for the unavailable state of the external electric power regardless of the detection of the coupling between the external connector C and the connector 27 is probably due to the switching off of the external device.

Figure 5A:
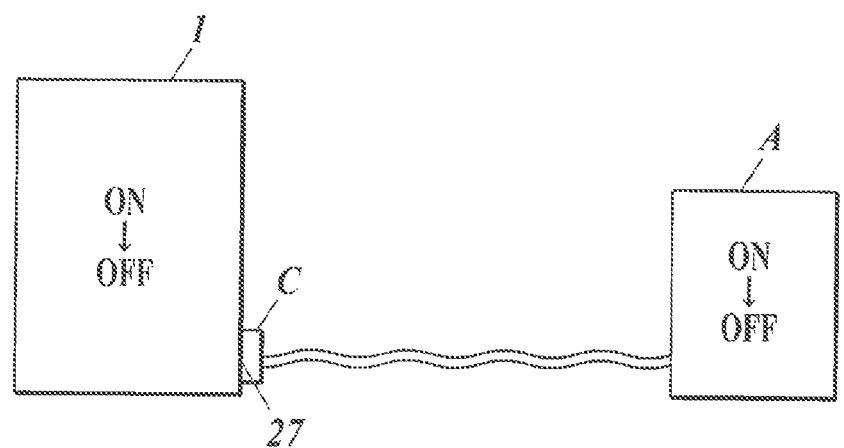
FIG. 5A illustrates cooperation between turning on/off of the radiographic image capturing apparatus and switching on/off of an external device.

In detail, under the condition illustrated in FIG. 5A where the radiographic image capturing apparatus 1 is connected to the external device A, the external connector C transmits the power-supply signal to the radiographic image capturing apparatus 1 while the external device A is being switched on. If the external device A is switched off, the external connector C transmits the supply-stop signal instead of the power-supply signal to the radiographic image capturing apparatus 1. In response to the reception of the supply-stop signal, the controller 22 of the radiographic image capturing apparatus 1 detects the change from the available state to the unavailable state of the external electric power.

Since the external connector C is coupled with the connector 27 of the radiographic image capturing apparatus 1 at the above timing, the controller 22 of the radiographic image capturing apparatus 1 detects the coupling at the above timing. Accordingly, the controller 22 turns off the radiographic image capturing apparatus 1 in the turned-on state, as described above. In this case, the radiographic image capturing apparatus 1 is turned off in cooperation with the switching off of the external device A, as illustrated in FIG. 5A. This configuration is the same as that of the conventional radiographic image capturing apparatus.

Such a configuration allows the radiographic image capturing apparatus 1 mounted on, for example, the capturing table in the capturing room or the cassette holder of the medical cart to be automatically turned off in cooperation with the switching off of the external device A. The radiographic image capturing apparatus 1 having such a configuration is friendly to the operator or radiological technician. The radiographic image capturing apparatus 1 mounted on, for example, the capturing table or cassette holder is automatically turned off even if the operator forgets to turn off the radiographic image capturing apparatus 1. Such automatic turning off of the radiographic image capturing apparatus 1 can prevent consumption of electric power in the built-in power source 24 (refer to FIG. 2) in the radiographic image capturing apparatus 1.

[Operation Upon Detachment of Radiographic Image Capturing Apparatus from Capturing Table]

Figure 5B:
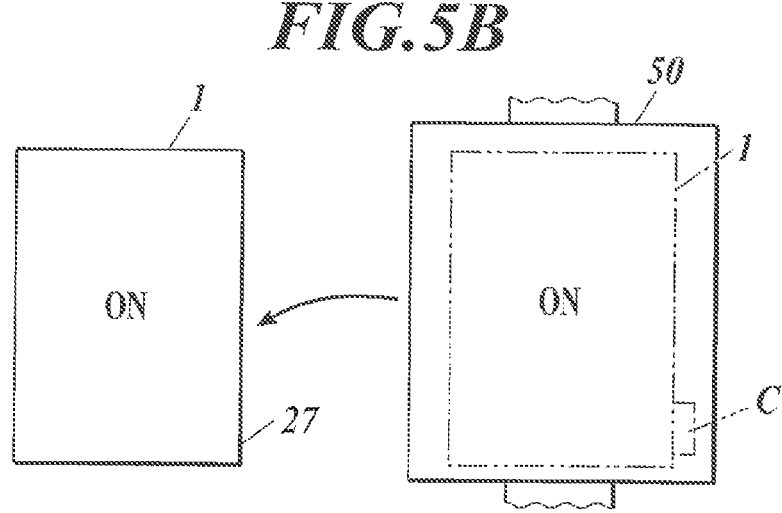
FIG. 5B illustrates the condition where the radiographic image capturing apparatus is detached from the capturing table.

If the radiographic image capturing apparatus 1 is in the turned-on state at the above timing when the controller 22 of the radiographic image capturing apparatus 1 detects the change from the available state to the unavailable state of the external electric power, the controller 22 of the radiographic image capturing apparatus 1 checks for coupling between the external connector C and the connector 27 of the radiographic image capturing apparatus 1, as described above. If the controller 22 detects the uncoupling between the external connector C and the connector 27 of the radiographic image capturing apparatus 1 as illustrated in FIG. 5B at the above timing, the reason for the unavailable state of the external electric power is probably due to the uncoupling of the external connector C from the connector 27 of the radiographic image capturing apparatus 1 and the detachment of the radiographic image capturing apparatus 1 from the capturing table by the operator or radiological technician for independent use of the radiographic image capturing apparatus 1.

In detail, while the radiographic image capturing apparatus 1 is mounted on the capturing table 50 and the connector 27 of the radiographic image capturing apparatus 1 is coupled with the external connector C of the capturing table 50, the external connector C of the capturing table 50 transmits the power-supply signal to the radiographic image capturing apparatus 1. When the radiographic image capturing apparatus 1 is detached from the capturing table 50 and the external connector C is uncoupled from the connector 27 of the radiographic image capturing apparatus 1 as illustrated in FIG. 5B, the external connector C transmits neither a power-supply signal nor supply-stop signal to the radiographic image capturing apparatus 1.

In response to the reception of neither a power-supply signal nor supply-stop signal, the controller 22 of the radiographic image capturing apparatus 1 detects the change from the available state to the unavailable state of the external electric power at the above timing.

Since the external connector C is uncoupled from the connector 27 of the radiographic image capturing apparatus 1 at the above timing, the controller 22 of the radiographic image capturing apparatus 1 detects the uncoupling at the above timing. Accordingly, the controller 22 maintains the turned-on state of the radiographic image capturing apparatus 1 (i.e., keeps the radiographic image capturing apparatus 1 turned on), as described above.

Accordingly, the radiographic image capturing apparatus 1 can maintain the turned-on state even after the detachment from the capturing table 50 as illustrated in FIG. 5B. The radiographic image capturing apparatus 1 can be independently used for radiographic image capturing without another turning-on operation on the radiographic image capturing apparatus 1 after the detachment from the capturing table 50.

In this case, the radiographic image capturing apparatus which is configured to be inevitably turned on/off in cooperation with the switching on/off of the external device A is turned off due to determining that the external device is switched off when actually the radiographic image capturing apparatus is detached for independent capturing. The operator or a radiological technician is thereby forced to turn on the radiographic image capturing apparatus again. This makes the operator to feel that the radiographic image capturing apparatus is difficult to use.

To address the problem, the radiographic image capturing apparatus 1 according to the embodiment maintains the turned-on state if the change from the available state to the unavailable state of the external electric power is due to the detachment of the radiographic image capturing apparatus 1 from the capturing table 50, as described above.

The operator or radiological technician therefore can detach the radiographic image capturing apparatus 1 from the capturing table 50 and use the radiographic image capturing apparatus 1 independently from the capturing table 50 for image capturing, without another turning-on operation on the radiographic image capturing apparatus 1. The radiographic image capturing apparatus 1 having such a configuration is friendly to the operator, leading to smooth radiographic image capturing with the radiographic image capturing apparatus 1.

It should be noted that the radiographic image capturing apparatus 1 according to the embodiment can maintain the turned-on state not only after the detachment of the turned-on radiographic image capturing apparatus 1 from the capturing table 50 but also after any event where the external connector C is detached from the connector 27 of the turned-on radiographic image capturing apparatus 1.

[Operation in Response to Turning on Operation on Radiographic Image Capturing Apparatus by Operator]

The conventional radiographic image capturing apparatus which is configured to be inevitably turned on/off in cooperation with the switching on/off of the external device may be automatically turned off in cooperation with the switching off of the external device connected to the radiographic image capturing apparatus, regardless of the manual turning-on operation on the radiographic image capturing apparatus by the operator or radiological technician, as described above.

To overcome such a disadvantage, the radiographic image capturing apparatus 1 according to the embodiment includes the controller 22 to conduct the determination of on/off control (in this case, the control to turn off the radiographic image capturing apparatus 1 in the turned-on state) to the radiographic image capturing apparatus 1 only at the above timing when the change from the available state to the unavailable state of the external electric power is detected, as described above.

Figure 5C:
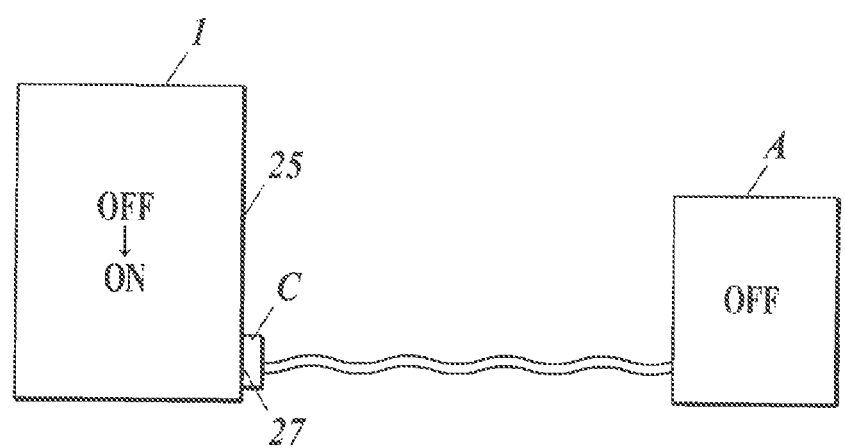
FIG. 5C illustrates the condition where the radiographic image capturing apparatus is turned on by an operator.

In detail, with reference to FIG. 5C, at the time when the radiographic image capturing apparatus 1 is turned on by the operator or radiological technician using, for example, the power switch 25 (refer to FIG. 1) of the radiographic image capturing apparatus 1, the external device A is in the switched-off state; therefore, the external connector C continues to transmit the supply-stop signal, and the controller 22 thus continues to detect the unavailable state of the external electric power. In other words, the controller 22 does not detect the change from the available state to the unavailable state of the external electric power.

The controller 22 of the radiographic image capturing apparatus 1 therefore does not conduct the determination of on/off control (in this case, the control to turn off the radiographic image capturing apparatus 1 in the turned-on state) to the radiographic image capturing apparatus 1 at the time when the radiographic image capturing apparatus 1 is turned on by the operator. Instead, the controller 22 turns off the radiographic image capturing apparatus 1 in accordance with the operation by the operator. Accordingly, the radiographic image capturing apparatus 1 according to the embodiment connected to the external device A in the switched-off state is properly turned on in accordance with the turning-on operation by the operator or radiological technician, as illustrated in FIG. 5C.

Since the radiographic image capturing apparatus 1 having such a configuration is prevented from being automatically turned off against the intention of the operator or radiological technician, the radiographic image capturing apparatus 1 is friendly to the operator. Such a radiographic image capturing apparatus 1 can be prevented from being automatically turned off in response to every turning-on operation on the radiographic image capturing apparatus 1 by the operator.

[Advantageous Effect]

As described above, if the external device is switched off under the condition where the external connector C is coupled with the connector 27 of the radiographic image capturing apparatus 1, the radiographic image capturing apparatus 1 according to the embodiment is turned off in cooperation with the switching off of the external device. In addition, if the radiographic image capturing apparatus 1 in the turned-on state is detached from the capturing table for independent use, for example, for placement on the body of a patient for radiographic image capturing, the radiographic image capturing apparatus 1 is not turned off but keeps the turned-on state.

Furthermore, if the radiographic image capturing apparatus 1 is turned on by the operator or radiological technician, the radiographic image capturing apparatus 1 is not automatically turned off in cooperation with the switched-off state of the external device but certainly turned on in accordance with the turning-on operation by the operator or radiological technician.

With the radiographic image capturing apparatus 1 according to the embodiment, a proper control can be achieved to turn off the radiographic image capturing apparatus 1 in the turned-on state depending on the situation, as described above. Such a radiographic image capturing apparatus 1 is friendly to the operator or radiological technician.

In the embodiment described above, the controller 22 of the radiographic image capturing apparatus 1 functions as a connector coupling detector to detect the coupling or the uncoupling between the external connector C and the connector 27 of the radiographic image capturing apparatus 1 and as a power supply detector to detect the available state or the unavailable state of the external electric power fed through the external connector C. Alternatively, the radiographic image capturing apparatus 1 may include a connector coupling detector and/or a power supply detector in addition to the controller 22.

[Modification 1]

In the embodiment described above, the radiographic image capturing apparatus 1 is turned off in cooperation with the switching off of the external device when the external connector C is coupled with the connector 27 of the radiographic image capturing apparatus 1. In this case, if a signal value D untransferred to the console or any other component is stored in the storage 23 (refer to FIG. 2) of the radiographic image capturing apparatus 1 at the time when the external device is switched off, the signal value D may be lost from the storage 23 upon the turning off of the radiographic image capturing apparatus 1.

To avoid the risk, the radiographic image capturing apparatus 1 according to Modification 1 has the following configuration: Upon the switching off of the external device, if the signal value D untransferred to the console or any other component is stored in the storage 23 of the radiographic image capturing apparatus 1, the controller 22 of the radiographic image capturing apparatus 1 can maintain the turned-on state of the radiographic image capturing apparatus 1, regardless of the detection of the coupling between the external connector C and the connector 27 of the radiographic image capturing apparatus 1, or without the detection of the coupling between the external connector C and the connector 27 of the radiographic image capturing apparatus 1.

Such a configuration can certainly prevent the loss of the signal value D stored in the storage 23 upon the automatic turning off of the radiographic image capturing apparatus 1 and eliminate the need for additional image capturing after the loss of the signal value D that may increase the exposed dose of the patient as the subject.

In Modification 1, the radiographic image capturing apparatus 1 or the console or any other component connected to the radiographic image capturing apparatus 1 should preferably be configured to notify the operator or radiological technician of the turned-on state of the radiographic image capturing apparatus 1 or the presence of untransferred signal value D in the storage 23 of the radiographic image capturing apparatus 1.

[Modification 2]

The external device may be temporarily switched off or may suspend power supply for any reason (for example, a temporal failure of or a temporal decrease in electric power), and then maybe immediately switched on or may restart the power supply.

According to the embodiments described above, the radiographic image capturing apparatus 1 is also turned off in response to the temporarily unavailable state of the external electric power if the external connector C is coupled with the connector 27. The operator or radiological technician, however, may be unaware of the turned-off state of the radiographic image capturing apparatus 1 and continue to use the radiographic image capturing apparatus 1 for radiographic image capturing.

To avoid the risk, the radiographic image capturing apparatus 1 according to Modification 2 has the following configuration: The controller 22 of the radiographic image capturing apparatus 1 does not immediately turn off the radiographic image capturing apparatus 1 at the above point when the coupling between the external connector C and the connector 27 of the radiographic image capturing apparatus 1 is detected. Instead, the controller 22 can maintain the turned-on state of the radiographic image capturing apparatus 1 for a predetermined time τ (for example, one minute) after the above timing. If the controller 22 detects the available state of the external electric power in response to, for example, the switching on of the external device or the restart of the power supply from the external device in the predetermined time $τ_r$, the controller 22 can maintain the turned-on state of the radiographic image capturing apparatus 1.

In this modification, the controller 22 can turn off the radiographic image capturing apparatus 1 after the predetermined time τ if the controller 22 does not detect the available state of the electric power fed from the external device in the predetermined time τ counted from the above timing.

[Control to Turn on Radiographic Image Capturing Apparatus in Turned-Off State]

Described above is the determination of the control to turn off the radiographic image capturing apparatus 1 in the turned-on state in response to the switching off of the external device A or after the detachment of the radiographic image capturing apparatus 1 from the capturing table 50.

The following description will focus on the determination of the control to turn on the radiographic image capturing apparatus 1 in the turned-off state.

As described above, the controller 22 of the radiographic image capturing apparatus 1 according to the embodiment includes a microcomputer (not shown) that can be driven with a low electric power from the built-in power source 24 in the radiographic image capturing apparatus 1 in the turned-off state. The controller 22 can turn on the radiographic image capturing apparatus 1 in the turned-off state even while the radiographic image capturing apparatus 1 is being turned off.

In this embodiment, if the controller 22 of the radiographic image capturing apparatus 1 detects the coupling between the external connector C and the connector 27 of the radiographic image capturing apparatus 1 at a second timing when the change from the unavailable state to the available state of the external electric power is detected, the controller 22 turns on the radiographic image capturing apparatus 1 in the turned-off state.

Herein, the control to turn off the radiographic image capturing apparatus 1 in the turned-on state is conducted at the "timing", whereas the control to turn on the radiographic image capturing apparatus 1 in the turned-off state is conducted at the "second timing". Such terms "timing" and "second timing" are used to avoid confusion therebetween.

Figure 6A:
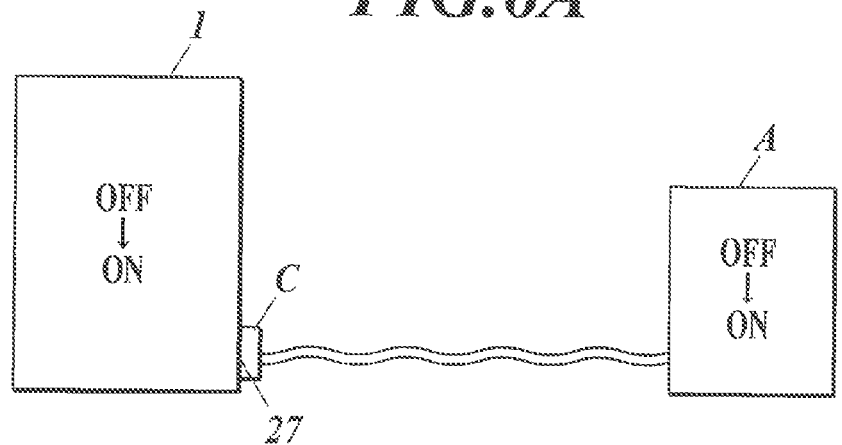
FIG. 6A illustrates cooperation between turning on/off of the radiographic image capturing apparatus and switching on/off of the external device.

In detail, if the external device A is switched on under the condition illustrated in FIG. 6A where the turned-off radiographic image capturing apparatus 1 is connected to the external device A (at the second timing), the external connector C transmits the power-supply signal instead of the supply-stop signal. In response to the power-supply signal, the controller 22 of the radiographic image capturing apparatus 1 detects the change from the unavailable state to the available state of the external electric power at the second timing.

Since the coupling between the external connector C and the connector 27 of the radiographic image capturing apparatus 1 is detected at the second timing, the controller 22 of the radiographic image capturing apparatus 1 turns on the radiographic image capturing apparatus 1 in the turned-off state. In this case, the radiographic image capturing apparatus 1 is turned on in cooperation with the switching on of the external device A as illustrated in FIG. 6A. This configuration is the same as that of the conventional radiographic image capturing apparatus described above.

Such a configuration allows the radiographic image capturing apparatus 1 mounted on, for example, the capturing table in the capturing room or the cassette holder of the medical cart to be automatically turned on in cooperation with the switching on of the external device A, such as a console or a relay, connected to the radiographic image capturing apparatus 1, without detachment of the radiographic image capturing apparatus 1 from the capturing table or the cassette holder of the medical cart. Such a radiographic image capturing apparatus 1 is friendly to the operator or radiological technician.

Figure 6B:
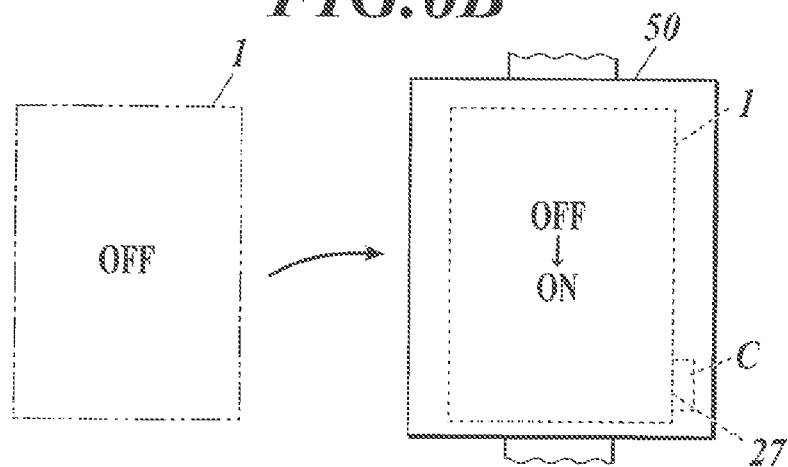
FIG. 6B illustrates the condition where the radiographic image capturing apparatus is mounted on the capturing table.

For example, mounting the turned-off radiographic image capturing apparatus 1 on the capturing table 50 and coupling the connector 27 of the radiographic image capturing apparatus 1 to the external connector C of the capturing table 50 as illustrated in FIG. 6B enable the external connector C that is transmitting neither a power-supply signal nor supply-stop signal to transmit the power-supply signal to the radiographic image capturing apparatus 1.

In response to the power-supply signal, the controller 22 of the radiographic image capturing apparatus 1 detects the change from the unavailable state to the available state of the external electric power at the second timing. Since the coupling between the external connector C (of the capturing table 50) and the connector 27 of the radiographic image capturing apparatus 1 is detected at the second timing, the controller 22 of the radiographic image capturing apparatus 1 turns on the radiographic image capturing apparatus 1 in the turned-off state.

Accordingly, the radiographic image capturing apparatus 1 can be automatically turned on simply by mounting the radiographic image capturing apparatus 1 in the turned-off state on the capturing table 50 (or simply by coupling the connector of the capturing table 50 to the connector 27 of the radiographic image capturing apparatus 1) as illustrated in FIG. 6B, without another turning-on operation on the radiographic image capturing apparatus 1. Such a radiographic image capturing apparatus 1 is friendly to the operator.

It should be noted that the radiographic image capturing apparatus 1 according to the embodiment is automatically turned on not only upon the mounting of the turned-off radiographic image capturing apparatus 1 on the capturing table 50 but also upon any event where the connector 27 of the radiographic image capturing apparatus 1 in the turned-off state is coupled to the external connector C of the external device A in the switched-on state.

Figure 6C:
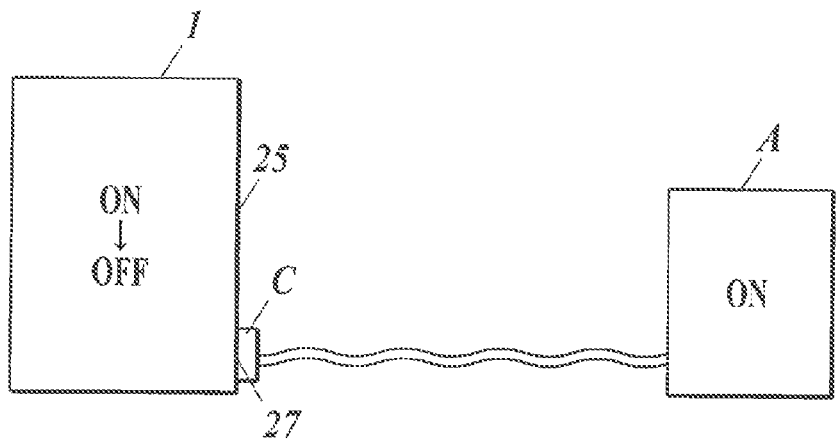
FIG. 6C illustrates the condition where the radiographic image capturing apparatus is turned off by the operator.

With reference to FIG. 6C, at the time when the turned-on radiographic image capturing apparatus 1 connected to the external device A is turned off by the operator or radiological technician using, for example, the power switch 25 (refer to FIG. 1) of the radiographic image capturing apparatus 1, the external device A is in the switched-on state; therefore, the external connector C continues to transmit the power-supply signal.

The controller 22 of the radiographic image capturing apparatus 1 therefore does not conduct the determination of on/off control (in this case, the control to turn on the radiographic image capturing apparatus 1 in the turned-off state) to the radiographic image capturing apparatus 1 at the time when the radiographic image capturing apparatus 1 is turned off by the operator. Instead, the controller 22 turns on the radiographic image capturing apparatus 1 in accordance with the operation by the operator. Accordingly, the radiographic image capturing apparatus 1 connected to the external device A in the switched-on state is properly turned off in accordance with the turning-off operation by the operator or radiological technician, as illustrated in FIG. 6C.

Since the radiographic image capturing apparatus 1 having such a configuration is prevented from being automatically turned on against the intention of the operator or radiological technician, the radiographic image capturing apparatus 1 is friendly to the operator. Such a radiographic image capturing apparatus 1 can be prevented from being automatically turned on in response to every turning-off operation on the radiographic image capturing apparatus 1 by the operator.

As described above, if the external device is switched on under the condition where the external connector C is coupled with the connector 27 of the radiographic image capturing apparatus 1, the radiographic image capturing apparatus 1 according to the embodiment is turned on in cooperation with the switching on of the external device. In addition, if the radiographic image capturing apparatus 1 in the turned-off state is mounted on the capturing table 50, the radiographic image capturing apparatus 1 is automatically turned on.

Furthermore, if the radiographic image capturing apparatus 1 is turned off by the operator or radiological technician, the radiographic image capturing apparatus 1 is not automatically turned on in cooperation with the switched-on state of the external device connected to the radiographic image capturing apparatus 1 but certainly turned off in accordance with the turning-off operation by the operator or radiological technician.

With the radiographic image capturing apparatus 1 according to the embodiment, a proper control can be achieved to turn on the radiographic image capturing apparatus 1 in the turned-off state depending on the situation, as described above. Such a radiographic image capturing apparatus 1 is friendly to the operator or radiological technician.

[Modification 3]

In the configuration in which the radiographic image capturing apparatus 1 is driven with the electric power from the built-in power source 24 (refer to FIG. 2) in the radiographic image capturing apparatus 1, if the electric power E (also represented by voltage V) stored in the built-in power source 24 is less than the lower limit $E_{min}$ capable of turning on and driving the radiographic image capturing apparatus 1, the controller 22 should not turn on the radiographic image capturing apparatus 1 regardless of the determination at the controller 22 to automatically turn on the radiographic image capturing apparatus 1.

In a preferred embodiment, if the electric power E stored in the built-in power source 24 is less than the lower limit $E_{min}$, the controller 22 of the radiographic image capturing apparatus 1 maintains the turned-off state of the radiographic image capturing apparatus 1, regardless of the detection of the coupling between the external connector C and the connector 27 of the radiographic image capturing apparatus 1 at the second timing described above, or without the detection of the coupling between the external connector C and the connector 27 of the radiographic image capturing apparatus 1.

In the preferred configuration, the controller 22 of the radiographic image capturing apparatus 1 may control to charge the built-in power source 24 with the electric power fed from, for example, the external device A through the external connector C. When the electric power E in the built-in power source 24 exceeds the lower limit $E_{min}$ and reaches a predetermined value sufficient for the image capturing, the controller 22 turns on the radiographic image capturing apparatus 1.

In the circumstance described above, if the operator or radiological technician tries to conduct the radiographic image capturing with the turned-off radiographic image capturing apparatus 1 under the misconception that the radiographic image capturing apparatus 1 is automatically turned on in cooperation with the switching on of the external device A as illustrated in FIG. 6A, or that the radiographic image capturing apparatus 1 is automatically turned on upon mounting of the radiographic image capturing apparatus 1 on the capturing table 50 as illustrated in FIG. 6B, the radiographic image capturing results in failure, which may cause the need for additional image capturing.

In a preferred embodiment to address the trouble described above, if the radiographic image capturing apparatus 1 should not be immediately turned on because the electric power E in the built-in power source 24 is less than the lower limit $E_{min}$, the controller 22 of the radiographic image capturing apparatus 1 notifies the operator or radiological technician of, for example, the execution of the electric charge of the built-in power source 24 or the turned-off state of the radiographic image capturing apparatus 1.

[Modification 4]

Figure 7:
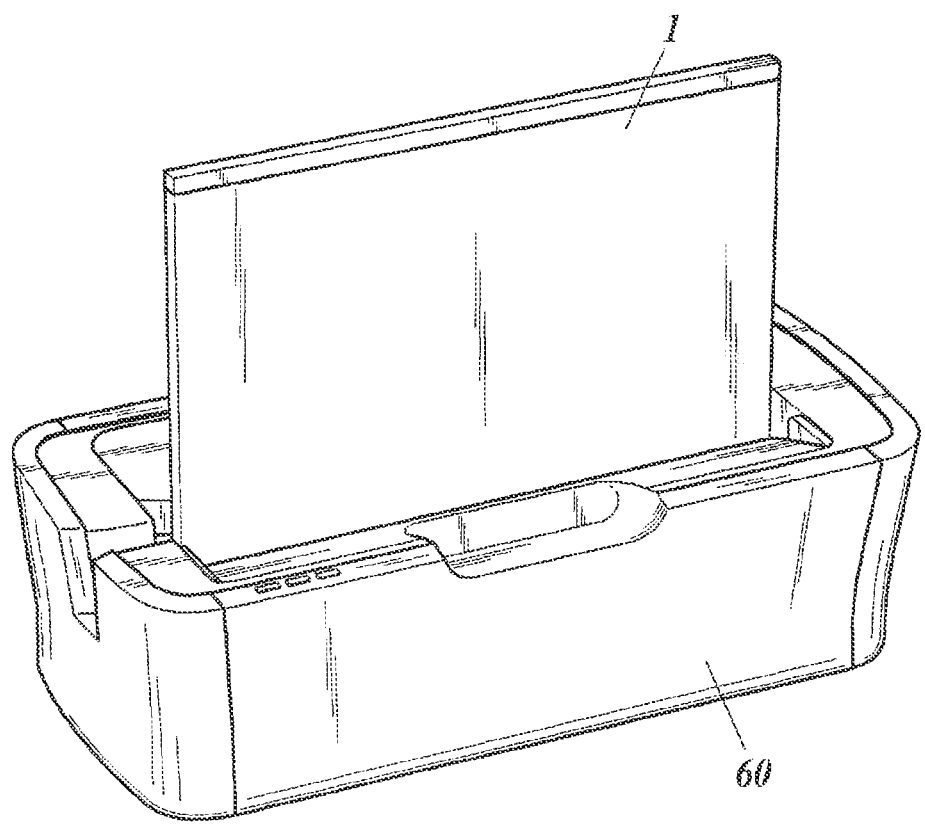
FIG. 7 illustrates the radiographic image capturing apparatus disposed in a cradle.

The radiographic image capturing apparatus 1 may be disposed in the cradle 60 to charge the built-in power source 24, as illustrated in FIG. 7. In this case, inserting the radiographic image capturing apparatus 1 in the cradle 60 automatically couples the connector 27 of the radiographic image capturing apparatus 1 to the external connector C of the cradle 60 (not shown).

The controller 22 of the radiographic image capturing apparatus 1 then conducts the control described above to turn on the radiographic image capturing apparatus 1 at a second timing when the cradle 60 is switched on (or when the start button (not shown) of the cradle 60 is held down and the external connector C of the cradle 60 transmits the power-supply signal instead of the supply-stop signal to the radiographic image capturing apparatus 1).

During the electric charge of the radiographic image capturing apparatus 1 with the cradle 60, however, the radiographic image capturing apparatus 1 should be kept in the turned-off state because the radiographic image capturing apparatus 1 is not used for the image capturing.

If the radiographic image capturing apparatus 1 is in the turned-on state during the electric charge of the radiographic image capturing apparatus 1 with the cradle 60, the radiographic image capturing apparatus 1 is driven with the electric power from the built-in power source 24 of the radiographic image capturing apparatus 1. In this state, the electric power in the built-in power source 24 is consumed while the built-in power source 24 is being charged with the cradle 60. This may increase the time required for the electric charge.

To avoid the disadvantage, when the external device A is a cradle, the controller 22 of the radiographic image capturing apparatus 1 should preferably maintain the turned-off state of the radiographic image capturing apparatus 1, regardless of the detection of the coupling between the external connector C (or the connector of the cradle 60) and the connector 27 of the radiographic image capturing apparatus 1 at the second timing when the change from the unavailable state to the available state of the external electric power from the external device A (in this case, cradle 60) is detected, or without the detection of the coupling between the external connector C and the connector 27 of the radiographic image capturing apparatus 1.

In addition, the controller 22 of the radiographic image capturing apparatus 1 can receive the ID, etc. for the cable and the external device A connected to the external connector C (which may be a connector of the cradle 60 or of any other device) from the external connector C coupled with the connector 27 of the radiographic image capturing apparatus 1. The ID, etc. for the cradle is preliminarily stored in the storage 23 (refer to FIG. 2) or a read-only memory (ROM) (not shown) of the radiographic image capturing apparatus 1 or is preliminarily written in a program for the radiographic image capturing apparatus 1.

The controller 22 of the radiographic image capturing apparatus 1 receives the ID from the external connector C when the connector 27 of the radiographic image capturing apparatus 1 is coupled to the external connector C. If the ID received from the external connector C is not for the cradle, the controller 22 conducts the control described above. If the ID received from the external connector C is for the cradle, the controller 22 can maintain the turned-off state of the radiographic image capturing apparatus 1.

Such a configuration allows the controller 22 of the radiographic image capturing apparatus 1, which is configured to conduct the control described above, to maintain the turned-off state of the radiographic image capturing apparatus 1 while the radiographic image capturing apparatus 1 is disposed in the cradle 60. This can reduce the time required for the electric charge and allows the operator or radiological technician to readily use the cradle 60 and the radiographic image capturing apparatus 1.

It should be understood that the embodiments and modifications described above are not construed to limit the present invention and can be appropriately modified without departing from the scope of the present invention.

The present U.S. patent application claims priority under the Paris Convention of Japanese Patent Application No. 2016-034024 filed on Feb. 25, 2016 the entirety of which is incorporated herein by reference.

What is claimed is:

1. A radiographic image capturing apparatus comprising:
   a two-dimensional array of radiation detecting elements;
   a connector couplable to an external connector;
   a connector coupling detector to detect coupling or uncoupling between the external connector and the connector of the radiographic image capturing apparatus;
   a power supply detector to detect an available state or an unavailable state of external electric power fed through the external connector; and
   a controller to control a turned-on state and a turned-off state of the radiographic image capturing apparatus, wherein
   at a timing when the power supply detector detects a change from the available state to the unavailable state of the external electric power, the controller turns off the radiographic image capturing apparatus in the turned-on state if the connector coupling detector detects the coupling between the external connector and the connector of the radiographic image capturing apparatus, or the controller maintains the turned-on state of the radiographic image capturing apparatus if the connector coupling detector detects the uncoupling between the external connector and the connector of the radiographic image capturing apparatus.

2. The radiographic image capturing apparatus according to claim 1, further comprising a storage to store signal values read from the radiation detecting elements, wherein
   at the timing, if untransferred signal values are stored in the storage, the controller maintains the turned-on state of the radiographic image capturing apparatus, regardless of the detection of the coupling between the external connector and the connector of the radiographic image capturing apparatus at the connector coupling detector, or without the detection of the coupling between the external connector and the connector of the radiographic image capturing apparatus at the connector coupling detector.

3. The radiographic image capturing apparatus according to claim 1, wherein
   the controller does not immediately turn off the radiographic image capturing apparatus at the timing if the connector coupling detector detects the coupling between the external connector and the connector of the radiographic image capturing apparatus, but turns off the radiographic image capturing apparatus in the turned-on state after a predetermined time from the timing if the power supply detector does not detect the available state of the external electric power in the predetermined time.

4. The radiographic image capturing apparatus according to claim 3, wherein
   if the power supply detector detects the available state of the external electric power in the predetermined time after the timing, the controller maintains the turned-on state of the radiographic image capturing apparatus.

5. The radiographic image capturing apparatus according to claim 1, wherein
   at a second timing when the power supply detector detects a change from the unavailable state of the external electric power to the available state of the external electric power, the controller turns on the radiographic image capturing apparatus in the turned-off state if the connector coupling detector detects the coupling between the external connector and the connector of the radiographic image capturing apparatus.

6. The radiographic image capturing apparatus according to claim 5, further comprising a connector identifier to identify if the external connector is a connector of a cradle, wherein
   at the second timing, if the connector identifier identifies the external connector as the connector of the cradle, the controller maintains the turned-off state of the radiographic image capturing apparatus, regardless of the detection of the coupling between the external connector and the connector of the radiographic image capturing apparatus at the connector coupling detector, or without the detection of the coupling between the external connector and the connector of the radiographic image capturing apparatus at the connector coupling detector.

7. The radiographic image capturing apparatus according to claim 5, further comprising a built-in power source to feed electric power to the controller, wherein
   at the second timing, if the electric power stored in the built-in power source is less than the lower limit capable of turning on the radiographic image capturing apparatus, the controller maintains the turned-off state of the radiographic image capturing apparatus, regardless of the detection of the coupling between the external connector and the connector of the radiographic image capturing apparatus at the connector coupling detector, or without the detection of the coupling between the external connector and the connector of the radiographic image capturing apparatus at the connector coupling detector.

* * * * *